United States Patent [19]

Timko

[11] Patent Number: 4,584,371

[45] Date of Patent: Apr. 22, 1986

[54] CATALYTIC PROCESS FOR PREPARING 3-ESTER-METHYL CEPHALOSPORINS FROM DESACETYL-7-AMINOCEPHALOSPORANIC ACID

[75] Inventor: Joseph M. Timko, Kalamazoo County, Mich.

[73] Assignee: The Upjohn Company, Kalamazoo, Mich.

[21] Appl. No.: 585,337

[22] Filed: Mar. 1, 1984

[51] Int. Cl.$^4$ ............................................. C07D 501/24
[52] U.S. Cl. ....................................... 544/16; 544/22; 544/26; 544/27; 544/30
[58] Field of Search ............................. 544/16, 22, 30

[56] References Cited

U.S. PATENT DOCUMENTS 3,948,906  4/1976  Eardley ................................. 544/22
4,008,231  2/1977  Wright .................................. 544/16
4,323,676  4/1982  Tsushima et al. ..................... 544/22

OTHER PUBLICATIONS

March, "Advanced Organic Chemistry", 2nd Ed., pp. 361 & 362 & 331.
J. of Med. Chem., 8, (1965), 174–181, "The Chemistry . . . Acetoxyl Replacements . . . Dithiocarbamates".
J. Chem. Soc., (London), (1965), Part IV, 5015–31, "Cephalosporanic . . . Nucleophiles", J. D. Cocker et al.
J. Chem. Soc., (London), (1965), Part IV, 7020–29, "Cephalosporanic . . . Mechanism", by A. B. Taylor.
Chem. Pharm. Bull. (Japan), 27(3), 696–702, (1979)–in English, "A New Route . . . Cephalosporins", by S. Tsushima et al.

Primary Examiner—Donald G. Daus
Assistant Examiner—Robert Benson
Attorney, Agent, or Firm—John T. Reynolds

[57] ABSTRACT 3-(Activated ester)methyl-3-cephem-4-carboxylic acids are prepared by the direct reaction of a 3-hydroxymethyl-3-cephem-4-carboxylic acid with an activated-O-ester-methyl forming acylating agent in the presence of a 4-(tertiary amino)pyridine catalyst, and an acid absorbing base, in a non-polar liquid solvent at $-78°$ C. to $+30°$ C.

5 Claims, No Drawings

CATALYTIC PROCESS FOR PREPARING 3-ESTER-METHYL CEPHALOSPORINS FROM DESACETYL-7-AMINOCEPHALOSPORANIC ACID

INTRODUCTION

This invention relates to processes for preparing activated cephalosporin intermediate compounds and to new cephalosporin intermediate compounds, per se. More particularly this invention provides an improved, direct process, involving the use of a catalyst, for converting a 3-hydroxymethyl-4-carboxy-$\Delta^3$-cephem cephalosporin compound to a 3-activated ester group-methyl-4-carboxy-$\Delta^3$- cephem cephalosporin intermediate, which intermediate products of this process are useful as further reactants in processes to make a large variety of known and new cephalosporin antibiotic compounds. Some of such 3-activated ester group-methyl compounds are new and are also claimed herein.

BACKGROUND OF THE INVENTION

The cephalosporin antibiotic art has developed over the past quarter century from Cephalosporin C and its nucleus, 7-aminocephalosporanic acid (7-ACA) to a great number of useful cephalosporin antibiotic compounds having a variety of substituent groups, mostly at the 3- and 7-positions of the 3-cephem ring system nucleus thereof. See the *Journal of the American Chemical Society*, (1962), 84, p. 3400 for the introduction of the "cepham" and "cephem" ring system nomenclature, now common in patents and literature in this art.

The early work in replacement of the 3-acetoxy group from Cephalosporin C, 7-ACA or other 3-acetoxymethyl-$\Delta^3$-cephem cephalosporin starting materials is well documented. For example, see "The Chemistry of Cephalosporins. IV. Acetoxyl Replacements with Xanthates and Dithiocarbames" by E. Van Heyningen, et al. in Journal of Medicinal Chemistry, 8, March, 1965, pp. 174–181; "Cephalosporanic Acids. Part III. Reactions with Pyridine - Kinetics and Mechanism" by A. B. Taylor in *Journal of the Chemical Society* (London), 1965, Part V, pp. 7020–7029; and "Cephalosporanic Acids. Part II. Displacement of the Acetoxy Group by Nucleophiles" by J. D. Cocker, et al. in *Journal of the Chemical Society* (London), 1965, Part IV, pp. 5015–5031.

More recently, efforts have been directed to studies of processes for preparing various cephalosporin compounds starting from 3-hydroxymethyl-$\Delta^3$-cephem 4-carboxylic acid compounds such as desacetylcephalosporin C. For example, Glaxo U.S. Pat. No. 3,948,906 describes preparation of monochloro-, dichloro and trichloroacetoxy groups on the 3-methyl carbon of the $\Delta^3$-cephalosporin by conversion of a 3-hydroxymethyl-7-protected amino-$\Delta^3$-cephem-4-carboxylic acid to a respective 4-carboxylic acid ester intermediate, which is then reacted at the 3-hydroxymethyl-position to form the respective 3-chlorinated acetoxy-methyl group, which reaction is then followed by a 4-de-esterification or de-protection step. However, such 3-activated ester-methyl process has the disadvantage of being multistep. More direct methods would be desirable. Unfortunately, prior processes which do not protect the $\Delta^3$-cephalosporin-4-carboxylic acid group are well known to produce substantial yield lowering quantities of the competing, undesired lactone by-product and/or by-products arising from $\Delta^3 \rightarrow \Delta^2$ double bond isomerization. The acid protecting group must be carefully chosen such that this $\Delta^3 \rightarrow \Delta^2$ isomerization does not occur during protection or deprotection. See also "A New Route to Semisynthetic Cephalosporins from Desacetylcephalosporin C. I. Synthesis of 3-Heterocyclicthiomethyl-cephalosporins" by S. Tsushima, et al. in *Chem. Pharm. Bull.* (Japan-in English), 27(3), pp. 696–702 (1979) disclosing the preparation of the 3-acetoacetoxymethyl-$\Delta^3$-cephem-4-carboxylic acid intermediate from the 3-hydroxymethyl-starting material, and Tsushima, et al., U.S. Pat. No. 4,323,676 which claims the process for preparing 3-acyloxymethyl-cephem compounds, with some defined carboxylic acid anhydrides. More importantly, this '676 patent sets forth in columns 1 and 2 thereof the prior problems which occurred in attempts to start with and process 3-hydroxymethyl-4-carboxy-$\Delta^3$-cephem acids to desired 3-nucleophile-methyl cephalosporin antibiotic end products. Yield lowering lactone formation occurred or there was a need to protect and later de-protect the 4-carboxyl group in reactions on the 3-hydroxyl methyl group of the starting material.

However, the 3-acetoacetoxymethyl group on the resulting cephalosporin intermediate compounds of the '676 patent are limited in their further utilities. It is well known that the more acidic the leaving group on the 3-hydroxymethyl group is, the more readily it is displaced by nucleophiles. Therefore, any ester whose corresponding acid is more acidic than acetic acid (pKa 4.75) will be a better leaving group than acetate, and, in particular, groups having a pKa of less than 4.0 are preferred. See the discussion in U.S. Pat. No. 3,948,906, top of column 2 and middle of column 3. The acetoacetic acid from the acetoacetyl group taught by the above Tsushima U.S. Pat. No. 9,323,676 has a pKa of about 3.6. Groups more acid are more preferable because they may be displaced more readily, e.g., under milder process conditions. Those in the cephalosporin chemical process arts continue to study to find process routes for the preparation in high yields of 3-(activated ester)-methyl-cephalosporin intermediate compounds having wider intermediate utility from 3-hydroxymethyl-3-cephem-4-carboxylic starting compounds, in overall processes for making a wide range of desirable 3-nucleophile-methyl cephalosporin antibiotic end products.

OBJECTS OF THE INVENTION

It is an object of this invention to provide an improved process for preparing 3-(activated ester-methyl)cephalosporin compounds from 3-hydroxymethyl-cephalosporin starting materials without the need for first protecting and later de-protecting the 4-carboxyl group of such compounds.

It is another object of this invention to provide a catalytic process for activating the 3-hydroxymethyl group of a desacetylcephalosporin starting compound with an activating group, to provide 3-activated ester-methyl-cephalosporin intermediate compounds having a wide range utility in subsequent processes for making a variety of known and new cephalosporin antibiotic end products.

Other objects, advantages and aspects of this invention will be apparent from reading the specification and the claims which follow.

SUMMARY OF THE INVENTION

Briefly, this invention provides an improved process for the Oacylation of the 3-hydroxymethyl group of a 7-(protected amino)-desacetylcephalosporanic acid, with an activating group whose corresponding acid is more acidic than acetic acid, that is, whose activating group acid has a pKa of less than pKa of 4.75, preferably less than 4.0. The activating ester groups may be in the form of an α-substituted acetate or α-substituted alkanoyl, a phenyl ring substituted benzoyl where the ring substituent can be any electron withdrawing group or atom such as chlorine or bromine, nitro, cyano, or the like, as well as an alkanesulfonyl, or -sulfinyl, arylsulfonic or -sulfinyl-group, without the need for prior 4-carboxyl group protection, and subsequent de-protection, by reacting the 7-(protected amino)-3-hydroxymethyl-3-cephem-4-carboxylic acid salt with a reactive derivative of such a low activated group containing pKa acid, in the presence of a 4-tert-aminopyridine catalyst, and an acid absorbing base at from above about $-78°$ C. to about 30° C., in a non-polar solvent containing mixture for a time sufficient to obtain the 3-(activated estermethyl)-cephem-4-carboxylic acid intermediate.

This invention also provides as new compounds, a group of preferred 7-{2-[N-(4-(4-$C_1$ to $C_3$-alkyloxybenzyloxy)carbonyl)imidazol-5-ylcarboxamido]-2-phenylacetamido-3-(activated ester group-methyl)-3-cephem-4-carboxylic acids, and salts thereof, where the 3-activated ester group is an acyl group whose corresponding acid is a substituted acetic or propionic acid having a pKa of less than about 4.0.

The end products of the above process, including the new compounds, are useful as chemical intermediates for the preparation of known and new end product cephalosporin antibiotic compounds such as the compound of detailed Example 10 of Yamada, et al. U.S. Pat. No. 4,217,450, and other 3-nucleophile-methyl cephalosporin antibiotics.

DETAILED DESCRIPTION OF THE INVENTION

One aspect of this invention provides an improved process for preparing a 3-(activated ester-methyl)-3-cephem-4-carboxylic acid, or salt thereof, of formula I (see attached Chemical Structure page) where R is an amino-protecting group;

$R_1$ is an alkali or alkaline earth salt forming cation; preferably an alkali metal cation; or is H $R_2$ is an activating acyl ester forming group whose corresponding activating group acid has a pKa of less than 4.75, preferably less than 4.0, more preferably less than 3.5;

Y is a group selected from the group consisting of —C(0)—, —S(0)$_2$—and —S(0)—;

which comprises reacting a 3-hydroxymethyl-3-cephem-4-carboxylic acid compound (II), where R, and $R_1$ are as defined hereinabove, with an acylating agent which is a reactive derivative of an $R_2$-Y-OH acid, of formula (III) or (IV), where, in formula III, X is chloride or bromide, Y is as defined above, and $R_2$ is as defined generally above, and, in formula (IV)

Y is as defined above, and each $R_2$ and $R_6$ can be the same, but preferably $R_2$ is the residue of desired activating ester group, whose acid has a pKa of less than 4.75, preferably less than 4.0, more preferably less than 3.5, and $R_6$ is a less expensive residue of an acid anhydride, that is, a mixed anhydride, preferably a branched chain $C_4$ to $C_6$-alkyl;

in the presence of a 4-tertiary aminopyridine catalyst, and in the presence of an acid absorbing base, at a temperature above about $-78°$ C. to about 30° C., preferably at from about $-55°$ C. to about 20° C., in a non-polar liquid solvent medium, for a time sufficient to form the 7-(protected-amino)-3-(activated ester-methyl)-3-cephem-4-carboxylic acid or salt compound (I).

The 3-hydroxymethyl-3-cephem-4-carboxylic acid starting materials are well known in the art, are readily available, or are easily obtained by known methods. Examples of compounds which can be used are desacetyl-Cephalosporin C, 7-(protected-amino)-3-hydroxymethyl-3-cephem-4-carboxylic acid, desacetyl-7-amino-3-cephem-4-carboxylic acid (desacetyl-7-ACA), desacetyl-cephalothin, and numerous other 3-hydroxymethyl-3-cephem-7-acylamido-4-carboxylic acid compounds. These 3-hydroxymethyl-3-cephem-4-carboyxlic acid starting compounds can be used in their free acid form, but are preferably used in salt form such as their potassium, sodium, lithium, magnesium chloride salts. The potassium salt form is preferred because its use increased solubility of the 3-hydroxymethyl-3-cephem-4-carboxylic compound in the non-polar solvent, thus enhancing the speed of the desired esterification reaction and minimizing formation of the undesired lactone byproduct.

"Salt forming cation" may be an alkali or alkaline earth metal. The salts may be formed by reacting the selected cephalosporanic acid with an appropriate base. Possible bases include metal hydrides such as sodium hydride or potassium hydride; metal hydroxides such as sodium hydroxide, potassium hydroxide, lithium hydroxide, magnesium hydroxide; metal alkoxides such as sodium methoxide, sodium ethoxide, potassium t-butoxide, lithium ethoxide, Grignard reagents such as methyl magnesium chloride or ethyl magnesium bromide; metal carboxylates of 2-ethylhexanoic acid, such a lithium-, sodium-, or potassium2-ethylhexanoate. The latter bases are preferred due to the mildness of the salt-forming conditions.

It is preferred that the starting 3-hydroxymethyl-3-cephem-4-carboxylic acid or salt thereof be as water free as is reasonably practicable since the more water that is present in the mixture the more activated acid derivative reactant (III) or (IV) is required to drive the desired 3-hydroxymethyl-cephalosporin esterification reaction to completion.

The activating esterifying agent reactant can be an acid halide (III) form of the $R_2$ groups listed above, preferably the chloride or bromide, and more preferably the chlorides of $C_2$ to $C_6$-halogenated alkanoic acids, e.g., α-chloroacetyl chloride,
α-chloropropionyl chloride,
α-chloro-n-butyryl chloride,
α-chloro-n-pentanoyl chloride,
α-chloro-n-hexanoyl chloride, and the brominated analogs of these listed acid chlorides, and their branched isomer forms, and commercial mixtures, where available, the dihalogenated $C_2$ to $C_6$-alkanoyl chlorides and bromides, e.g.,
α-dichloroacetyl chloride,
α-dichloropropionyl chloride,
α-dichlorobutyryl chloride,
α-dichloropentanoyl chloride,
α-di-chlorohexanoyl chloride,
and their brominated analogs and branched chain isomers, and commercial mixture forms, where available, and trichloroacetyl chloride and tribromacetyl bromide, and commercial mixtures thereof, where applicable as well as $C_6$ to $C_{12}$-aromatic group containing carboxylic chlorides and bromides, e.g.,
benzoyl chloride,
o-chlorobenzoyl chloride,
m-chlorobenzoyl chloride,
p-chlorobenzoyl chloride,
2,4- and 3-, 5-dichlorobenzoyl chloride,
mixed chlorinated benzoyl chloride and their brominated analogs, as well as related aromatic compounds such as o-, m- and p-toluoyl chloride,
dimethylbenzoyl chloride,
biphenylylcarbonyl chloride
1- and 2-naphthylcarbonyl chloride, their brominated analogs, and the like.

Activating ester forming reactants also include the $C_1$ to $C_6$-alkanesulfonic and -sulfinic acid, chlorides and bromides, e.g.,
methanesulfonyl chloride,
ethanesulfonyl chloride,
n-propylsulfonyl chloride,
isopropylsulfonyl chloride,
n-butylsulfonyl chloride,
isobutylsulfonyl chloride,
tert-butylsulfonyl chloride,
pentanesulfonyl chloride isomers,
hexanesulfonyl chloride isomers,
methanesulfinyl chloride,
ethanesulfinyl chloride,
n-propylsulfinyl chloride,
isopropylsulfinyl chloride,
n-butylsulfinyl chloride,
isobutylsulfinyl chloride,
tert-butylsulfinylsulfinyl chloride,
pentanesulfinyl chloride isomers,
hexanesulfinyl chloride isomers,
and their brominated analogs, branched chain isomers and commercial mixture forms,
the $C_6$ to $C_{12}$-aromatic hydrocarbon and halogenated aromatic hydrocarbon sulfonyl and -sulfinyl chlorides and bromides, e.g.,
benzenesulfonyl chloride,
chlorobenzenesulfonyl chloride,
dichlorobenzenesulfonyl chloride,
trichlorobenzenesulfonyl chloride,
pentachlorobenzenesulfonyl chloride,
toluenesulfonyl chloride,
chlorinated toluenesulfonyl chloride,
xylenesulfonyl chloride,
chlorinated xylenesulfonyl chloride,
trimethylbenzenesulfonyl chloride,
chlorinated trimethylbenzenesulfonyl chloride,
1- and 2-naphthanesulfonyl chloride,
1-biphenylsulfonyl chloride,
chlorinated-1-biphenylsulfonyl chloride,
and $C_6$ to $C_{12}$-aromatic hydrocarbon and halogenated $C_6$ to $C_{12}$-aromatic hydrocarbon brominated analogs and -sulfinyl chloride and bromide analogs of the above compared, e.g.,
benzenesulfonyl bromide,
benzenesulfinyl bromide,
toluenesulfinyl bromide,
and the like.

The activating esterifying reagent can also be an anhydride or mixed anhydride of the acid which provides the desired activatedester-methyl group on the methyl carbon atom in the 3-position of the cephem ring structure.

Examples of anhydride forms of the activating ester forming reactants which can be used include the anhydrides of the halogenated $C_2$ to $C_6$-alkanoic acids such as
chloroacetic anhydride,
α-chloropropionic anhydride,
α-chloro-n-butyric anhydride,
α-chloro-n-pentanoic anhydride,
α-chloro-n-hexanoic anhydride,
their brominated analogs, and their branched chain isomers, the benzoic anhydride, chlorinated benzoic anhydride, their brominated analogs, and the like, and mixed anhydride forms of the desired activating acylating acid such
chloracetic trimethylacetic,
α-chloropropionic trimethylacetic,
α,α-dichloropropionic pivalic,
chloroacetic isobutyroyl,
α-chloropropionic isobutyroyl,
trichloroacetic isobutyroyl,
anhydrides, their brominated analogs, and isomeric forms, and the like.

Other useful acid halides and anhydrides having similar pKa properties such as cyanoacetyl chloride, phenoxyacetyl chloride, nitroacetyl chloride and the reactive derivatives of the acids having pkas below 4.75, preferably below 4.0, set forth in U.S. Pat. No. 3,948,906, column 3, 11, 54 to 68, and the like, could also be used to form these desired activated ester intermediate cephalosporin compounds in the process of this invention. However, the economical chlorinated acetyl and α-halogenated propionyl chlorides are preferred for use herein for reasons of ready availability, cost and versatility of the resulting ester in further processing to make useful end product cephalosporin antibiotic compounds.

The 4-(tertiary amino)pyridine catalyst used in the process of the invention

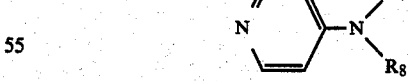

preferably has a molecular weight below about 170 and can be for example, where each of $R_7$ and $R_8$ is a $C_1$ to $C_3$-alkyl to provide
a 4-(bis-$C_1$ to $C_3$-alkylamino)pyridine such as
4[(N,N-dimethyl)amino]pyridine, (DMAP)
4[(N,N-diethyl)amino]pyridine,
4[(N,N-di-n-propyl)amino]pyridine,
4[(N,N-di-isopropyl)amino]pyridine,
4[(N-methyl-N-ethyl)amino]pyridine,
4[(N-ethyl-N-propy)lamino]pyridine,
and the like, and 4-aminopyridine compounds where the $R_7$ and $R_8$ are a series of methylene (—$CH_2$—) groups taken together with the nitrogen to which they are bonded to complete a ring having 4 to 5 ring carbon atoms therein, thus being for example 4-(N-piperidinyl)pyridine, and
4-(N-pyrrolidinyl)pyridine, or the like. The commercially available 4-[(N,N-dimethyl)amino]pyridine (DMAP) has been found to be eminently suitable as the catalyst for this reaction and is preferred herein. The 4-(N-pyrrolidinyl)pyridine is also commercially available, but is more expensive.

The catalyst can be added to the reaction mixture at any time as the reaction mixture is being prepared. We prefer to add the catalyst to the solution or mixture of the 3-hydroxymethyl-7-protected amino-3cephem-4-carboxylic acid or salt thereof in the selected non-polar solvent, say, methylene chloride, in an amount up to about 1 molar equivalent of the catalyst relative to the concentration of the 3-hydroxymethyl-cephalosporin reactant in the mixture. Generally, it is sufficient to provide from about 0.1 to about 0.5, preferably about 0.2–0.25 molar equivalents of the catalyst to the reaction mixture, based upon the molar concentration of the 3-hydroxymethyl-cephalosporin reactant in the mixture.

An acid absorbing base, preferably an economical tertiary amine, such as a tris ($C_1$ to $C_3$-alkyl)amine, e.g., trimethylamine, triethylamine, tripropylamine, or as an aromatic tertiary amine such as N,N-dimethylaniline, and the like, is added to the reaction mixture to neutralize the by-product acid formed in the acylation/esterification reaction process of this invention. Since one mole of acid, e.g., hydrogen chloride, is formed per mole of product, the amount of acid absorbing base, e.g., a trialkylamine such as triethylamine, added should be equal to or in slight excess of the amount of the above acid halide reactant added to the mixture.

The reaction mixture of the selected 3-hydroxymethyl-3-cephem-4carboxylic acid or salt (II), the catalyst, the acid absorbing base is preferably formed and left stirring, or otherwise agitating, in the cold, that is, below 30° C., preferably below 20° C., ideally at about −20° C. to about −0° C. in a non-polar, organic liquid solvent, such as a chlorinated $C_1$ to $C_2$-alkane, e.g., methylene chloride, chloroform, carbon tetrachloride, ethylene dichloride, and the like, tetrahydrofuran, diethyl ether, hexane, heptane, octane, cyclohexane or mixtures thereof until the 3-hydroxymethyl group esterification reaction is efficiently complete. This catalyzed reaction usually proceeds quickly at preferred temperatures, e.g., in less than 5 minutes at −20° C., much slower at −55° C. and is not observable at −78° C. Because of potential competing side reactions, it is not recommended to add the acid chloride or bromide reactant and the acid absorbing base to the reaction mixture in a pre-mixed solution. The timing and rate of addition of the acid absorbing base can be varied, but optimum process conditions ultimately depend upon the amount of water present in the reaction mixture. The acid absorbing base and the acid derivative (III) or (IV) reactant can be added to the reaction mixture separately but simultaneously, or the addition may be done sequentially, e.g., 1 equivalent of the acid absorbing base, followed by addition of 1.0 equivalent of the activating agent reactant over 5 to 20 minutes to the dissolved 3-hydroxymethyl-7-amino-3-cephem-4-carboxylic acid potassium salt and catalyst in the non-polar solvent, followed by addition of a second equivalent of the acid absorbing base, e.g., triethylamine, followed by addition of a second equivalent of the activating agent reactant to ensure complete reaction of the 3-hydroxymethyl-3-cephem-4-carboxylic acid or salt reactant in the mixture. Samples of the reaction mixture can be taken periodically and analyzed by conventional methods, such as by high performance liquid chromatography (HPLC) methods to determine the amount of the unreacted 3-hydroxymethyl-3-cephem-4-carboxylic acid reactant still present in the mixture, and which analysis also indicates the extent of completion of the activation reaction.

The resulting 3-(activated ester-methyl)-cephalosporin product of this process can then be recovered from the resulting reaction mixture by conventional means, washed, dried and stored until ready for use in further processing to make 3-(nucleophile-methyl)-cephalosporin antibiotic end product.

We suggest here several possible methods for extracting the product from the reaction mixture, the first of which we prefer, due mainly to the physical parameters of our product.

(1) Quench the reaction mixture into aqueous strong acid, e.g., hydrochloric, sulfuric or ortho-phosphoric, etc. acid, and then isolate the 3-(activated ester-methyl)-cephalosporin intermediate product as the solid cephalosporanic acid.

(2) Quench the reaction mixture into hexane, or a commercially equivalent hydrocarbon mixture, e.g., Skellysolve B ® brand of mixed hexanes to get a total recovery or "knockout" of salts in the mixture including inorganic salts and organic salts including cephalosporin salts.

(3) Quench the reaction mixture in a pH 5 to 6 buffered aqueous solution, to remove organic and inorganic salts, and then quench the separated organic liquid layer into hexane to recover the cephalosporin salts.

This process has been studied primarily in connection with our goal of efficiently preparing 3-(activated ester)-methyl)-7-β{D-α[4-(4-methoxybenzyloxy)carbonylimidazolyl-5-carboximido]phenylacetamido}-3-cephem-4-carboxylic acid, which intermediate compounds are useful for preparing 3-[(4-β-sulfo-ethyl-pyridinium)methyl]-7-β-[D-(−)-α[(4-carboxyimidazole-5-carboxamido]phenylacetamido]-3-cephem-4-carboxylic acid, and pharmaceutically useful salts thereof. This cephalosporin antibiotic end product is useful and claimed per se in Yasuda, et al. U.S. Pat. No. 4,217,450, particularly detailed Example 10 thereof.

Another aspect of this invention provides a group of compounds of structure (V), which are new. They are all useful as chemical intermediates in chemical processes for making a variety of useful end product—3-(nucleophile-methyl)-cephalosporins, but are of particular interest to us for use as intermediates to make the end product cephalosporin antibiotic referred to above, in U.S. Pat. No. 4,217,450, Example 10.

In the new compound structures (V), $R_1$ is hydrogen, or a salt forming cation, preferably an alkali metal such as sodium, potassium, or an alkaline earth metal mixed salt, such as, a magnesium chloride salt, $R_2$ is a residue ester group from α-substituted acetic acid or α-substituted propionic acid having a pKa of less than 4.0, and $C_1$ to $C_3$-alkyl means methyl, ethyl or propyl, including isopropyl.

Examples of such compounds include those of formula V wherein:

$R_1$ is H or an alkali metal; $R_2$ is selected from the group consisting of monochloroacetyl,
dichloroacetyl,
trichloroacetyl,
α-chloropropionyl,
α,α-dichloropropionyl,
cyanoacetyl,
phenoxyacetyl, and the $C_1$ to $C_3$-alkyl group is methyl.

These new compounds (V) can be prepared by the process described hereinabove, and as exemplified in the detailed examples which follow, using a reactive derivative of the selected acid, e.g., reactant forms (III) or (IV) referred to hereinabove, wherein $R_2$ is the selected residue ester group from the α-substituted acetic acid or α-substituted propionic acid having a pKa of less than 4.0.

The invention is further illustrated and exemplified by the detailed examples which follow, which are not intended as being limiting. All temperatures are in degrees Centigrade unless otherwise indicated, $CH_2Cl_2$ means methylene chloride, THF means tetrahydrofuran, DMF means N,N-dimethyl formamide, $SO_2$ means sulfur dioxide, HCl means hydrogen chloride, $H_2O$ means water, t-BuOK means potassium tert-butoxide, TEA means triethylamine, DMAP means 4-(N,N-dimethylamino)pyridine, DCAC means dichloroacetyl chloride, HPLC means high performance liquid chromatography analysis, $N_2$ means nitrogen gas, $H_3PO_4$ means orthophosphoric acid, PESA means 2-(4-pyridinyl)ethanesulfonic acid, $NaHCO_3$ means sodium bicarbonate, NaPESA means sodium 2-(4-pyridinyl)ethanesulfonate.

EXAMPLE 1

A. Preparation of 5,10-dioxo-5H, 10H-diimidazo[1,5-a:1',5'-d]pyrazine-1,6-dicarbonyl dichloride.

A slurry of 72.0 g. (0.46 mole) of imidazole-4,5-dicarboxylic acid (IDC) in 425 ml. of methylene chloride and 10 ml. of DMF was stirred under nitorgen at room temperature. To this slurry was added slowly 225 ml. of thionyl chloride. The resulting slurry was heated at reflux for 6 hours. At the end of the reflux period the evolution of $SO_2$ and HCl had ceased. The reaction mixture was cooled to room temperature and filtered. The solids were washed with methylene chloride and dried on the filter in a nitrogen dry box for 2 hours. The solids were then dried under vacuum at 25° C. to give 68.9 g. (0.22 mole)(95.4% chemical yield)(95.7% weight yield) of 5,10-dioxo-5H-,10H-diimidazo-[1,5-a:1',5'-d]pyrazine-1,6-dicarbonyl dichloride (IDCD-Cl).

B. Preparation of 5,10-5H,10H-diimidazo[1,5-a:1',5'-d]pyrazine1,6-bis(4-methoxybenzyloxy carbonyl ester).

A slurry of 25.0 g. (0.08 mole) of dichloride from part A, hereinabove in 300 ml. of THF was stirred at 19° C. in a water bath. To this slurry was added 30 ml. [33.24 g. (0.24 mole)] of p-methoxybenzyl alcohol. The resulting slurry was stirred at 19° C. for 30 minutes. To this slurry was added a solution of 12.9 ml. [12.642 g. (0.16 mole)] of pyridine in 50 ml. of tetrahydrofuran over a period of 30 minutes. The resulting slurry was stirred overnight (17 hours) at 19° C. This slurry was filtered. The solids were washed with 250 ml. of methanol and dried under vacuum at 40° C. to give 40.5 g. (0.078 mole)(98.2% chemical yield)(162% weight yield) the above-named bisester.

C. Preparation of 2-[N-(4-methoxybenzyloxycarbonyl] imidazol-5-ylcarboxamido]-2-phenylacetic acid.

A slurry of 17.5 g. (0.034 mole) of the bis-ester from part B hereinabove and 10.245 g. (0.068 mole) of D-phenylglycine in 105 ml. of formamide and 18.92 ml. [13.715 g. (0.14 mole)] of triethylamine was stirred at room temperature (21° C.) overnight (17 hours). The resulting solution was filtered over a filter aid (Celite ®). The cake was washed with 150 ml. of water. Another 350 ml. of water were added to the filtrate. The pH of the filtrate was lowered to pH 2 by the slow addition (3 hours) of about 2.5 ml. of 6N aqueous hydrochloric acid. The resulting slurry was filtered. The solids were washed with water and dried under vacuum at 40° C. to give 25.913 g. (0.063 mole)(93.4% chemical yield)(148.1% weight yield) of the herein-named N-substituted-phenylglycine.

A 20 g. portion of the N-substituted-phenylglycine from the above run was dissolved in 1 liter of 42% methanol/58% methylene chloride at reflux. The resulting solution was concentrated at atmospheric pressure on a steam bath. When the pot temperature reached 55° C., 200 ml. of methanol was added and the slurry was concentrated to a volume of 100 ml. under vacuum. This slurry was cooled at 0°-5° C. for 1 hour and filtered. The solids were washed with methanol and dried under vacuum at 40° C. to give 17.02 g. (85.1% recovery) of the sub-titled N-substituted-phenylglycine, m.p. 176°-177.5°, $[\alpha]^{25} -53.5°$ C. (C 1.0%, pyridine) overall yield, 79.5% Chemical (126.0% weight).

D. Preparation of a 7-{β-[D-α-[4-(4-methoxybenzylcarbonyl)imidazolo-5-carboxyamido]-α-phenylacetamido}-3-hydroxymethyl-3-cephem-4-carboxylic acid.

A slurry of 5.902 g. (0.0256 mole) of 7-amino-3-desacetyl-3-cephem-4-carboxylic acid(7-aminocephalodesic acid) in 30 ml. of acetonitrile was stirred under nitrogen at room temperature. To this stirred slurry there was added 22.0 ml. (20.06 g. - 0.116 mole) of 2-trimethylsilyloxy-2-penten-4-one. This resulting slurry mixture was stirred at 35°-36° C. for 3 hours to form a 3,4-bis(-trimethylsilyl)-7-amino-3-cephem-4-carboylate intermediate.

In a separate vessel, 10.0 g. (0.0244 mole) of 2-[N-[4-(4-methoxybenzyloxycarbonyl)]-5-imidazolocarbonyl]-2-phenylacetic acid intermediate and 80 ml. of acetonitrile were stirred under a nitrogen atmosphere at room temperature. To this slurry there was added 3.12 ml. (2.544 g. - 0.0256 mole) of N-methylpiperidine. The resulting solution was cooled to −20° C. To this resulting −20° C. cooled solution there was added 3.78 ml. (3.969 g. - 0.029 mole) of isobutylchloroformate all at once, to form the intermediate 2-{-N-[4-(4-methoxybenzyloxycarbonyl)-imidazol-5-ylcarboxy]-2-pheny}lacetic isobutyloxycarbonyl mixed anhydride intermediate.

The immediately above mixed anhydride solution was stirred at −20° C. for 15 to 30 minutes to ensure complete reaction and maximum homogeneity of the solution mixture. To this stirred solution there was added the above-described mixture of the 7-amino-3,4-bis(trimethylsilyl)-3-hydroxymethyl-3-cephem-4-carboxylic acid in acetonitrile. During this addition the reaction vessel pot temperature was kept between −10° C. and −20° C. The resulting stirred reaction mixture was allowed to warm to 0° C. and then stirred at about 0° C. for 3 hours. Water (7.9 ml. - 0.439 mole) was then added to this stirred mixture. On addition of the water the reaction mixture turned red and after one minute a thick slurry formed. After stirring for an additional minute the reaction mixture was diluted with 50 ml. of acetonitrile to facilitate stirring. After stirring the mixture for another 10 minutes, the slurry was filtered. The solids were washed with 250 ml. of acetonitrile and then dried on the filter in a dry box overnight to give 12.76 g. (0.021 mole), 80.1% chemical yield, of intermediate 3-hydroxymethyl-7-[2-(N-(4-(4-methoxybenzyloxycarbonyl)imidazol-5-ylcarboxylamido)-2-phenylacetamido]-3-cephem-4-carboxylic acid.

E. DMAP Catalyzed Production of a 3-dichloroacetyloxymethyl-7-β-{D-α-[4-(4-methoxybenzyloxycarbonyl)imidazoyl-5-carboxamido]-α-phenylacetamido}-3-cephem-4-carboxylic acid.

To a dry 1-liter, 3-neck, jacketed round bottom flask under a $N_2$ atmosphere and containing 24.8 g. of 3-hydroxymethyl-7β-{D-α-[4-(4-methoxybenzyloxy)carbonylimidazolyl-5-carboxamido]phenylacetamido}-3-cephem-4-carboxylic acid (40 mmoles) there was added 300 ml. of $CH_2Cl_2$ and 20 ml. of THF. The resulting slurry was cooled to −10° C. and 40 mmoles of t-BuOK was added slowly over 10 minutes as 24.8 ml. of a 1.62M t-BuOK solution in THF. After addition of the t-BuOK was complete, the slurry was stirred at −10° C. for an additional 30 minutes and the slurry was cooled to −20° C. Then one equivalent of TEA (5.58 ml.) was added along with 0.2 equivalents of DMAP (0.98 g.). Then slow addition of 1.0 equivalent of DCAC in $CH_2Cl_2$ was begun (3.85 ml. of DCAC in 18 ml. of $CH_2Cl_2$ solution). The addition was completed over 13 minutes. Then 0.5 equivalent of TEA was added (2.8 ml.), 0.5 ml. of the DCAC/$CH_2Cl_2$ solution (1.9 ml. of DCAC in 9 ml. of $CH_2Cl_2$ solution) was added over 7 minutes. Then another 0.5 equivalent of TEA (2.8 ml.) was added, followed by another 0.5 equivalent of DCAC solution (1.9 ml. of DCAC in 9 ml. of $CH_2Cl_2$) over 7 minutes. After stirring for five minutes a sample of the reaction mixture was extracted for HPLC analysis.

In 13 minutes of reaction time it was determined that the 3hydroxymethyl cephalosporin starting material was less than 5% of the reaction mixture so the reaction mixture was quenched into an aqueous $H_3PO_4$ solution (360 ml. $H_2O$ plus 40 ml. of 1M $H_3PO_4$) containing hexane (80 ml.). The solids were filtered.

The filtered solid was washed with 20% V/V hexane in $CH_2Cl_2$ mixture and dried by pulling $N_2$ through the filter to give 32.82 g. of 3-(dichloroacetyloxymethyl)-7-β-{D-α-[4-(4-methoxy-benzyloxycarbonyl)-imidazolyl-5-carboxamido]phenylacetamido}-3-cephem-4-carboxylic acid solid product (HPLC assay indicates the product contains 77% by weight of the named solid product). The NMR analysis ($CDCl_3$-DMSO-$d_6$) of the product consisted of resonances at the following chemical shifts (ppm downfield from TMS): 3.3(m), 3.7(s), 4.8(d), 5.0(m, 3'-CH$_2$), 5.2(s), 5.6(m), 5.8(d), 6.3(s, CHCl$_2$), 6.7(d), 7.1-7.8(m), 9.3(d), 10.6(d). This material was carried on to make the cephalosporin antibiotic, 7-β-{D-α[4-(4-carboxyimidazole-5-carboxamido)-α-phenyl]acetamido}-3-(4-β-sulfoethylpyridinium)methyl-3-cephem-4-carboxylic acid.

EXAMPLE 2

3-(Dichloroacetoxymethyl)-7-β-{D-α-[4-(4-methoxybenzyloxycarbonyl)imidazole-5-carboxyamido]-α-phenylacetamido}-3-cephem-4-carboxylic acid.

To a dry flask under $N_2$ atmosphere there was added 30 ml. of THF, 0.54 ml. of $H_2O$ (30.0 mmole) and 300 ml. of $CH_2Cl_2$, and then the resulting mixture was cooled to 0° C. To the cooled solution there was added, dropwise over 6 minutes, 18.51 ml. of t-BuOK/THF solution (1.62M t-BuOK, 30 mmoles, 1.0 equivalent to the 3-hydroxymethyl cephalosporin starting material) which addition resulted in formation of a very fine suspension of solid KOH. The resulting slurry was cooled to −20° C. and then 18.5 g. (30 mmoles) of solid 3-hydroxymethyl-7-β-{D-α-[4-(4-methoxybenzyloxycarbonyl)imidazole-5-carboxamido]-α-phenylacetamido}-3-cephem-4-carboxylic acid starting material was added. After stirring the mixture at −20° C. for 30 minutes, 0.75 g. of DMAP (6.14 mmoles) was added, followed by 4.2 ml. of TEA (30 mmoles) and then 1.0 equivalent of DCAC solution in $CH_2Cl_2$ was added over 3 minutes (2.89 ml. of DCAC in 30 ml. of $CH_2Cl_2$). A second equivalent of TEA (4.2 ml.) was then added followed by addition of a second equivalent of DCAC solution (2.89 ml. of DCAC in 30 ml. of $CH_2Cl_2$) over 5 minutes. After stirring the mixture for an additional 10 minutes at −20° C., a sample thereof was withdrawn for HPLC analysis. When HPLC analysis of samples of the reaction mixture indicated that less than 5% of the above 3-hydroxymethyl cephalosporin starting material remained, the reaction mixture solution was quenched into an aqueous solution containing 32.5 mmoles of $H_3PO_4$ (360 ml. $H_2O$ plus 32.5 ml. of a 1M $H_3PO_4$ solution, at room temperature) and stirred for 10 minutes. The resulting quenched mixture was then filtered, and then washed with 20 ml. of $H_2O$, 20 ml. of $CH_2Cl_2$, and then dried to obtain the 3-(dichloroacetoxymethyl)-7-β-{D-α-[4-(4-methoxybenzyloxy)carbonyl]imidazole-5-carboxamido]-α-phenylacetamido}-3-cephem-4-carboxylic acid, as a dry powder, 16.3 g., 74% theoretical (chemical) yield.

EXAMPLE 3

Preparation of 3-(4-β-sulphoethylpyridiniummethyl)-7-β-{D-α-[4-(4-methoxybenzyloxy)carbonyl]imidazole-5-carboxamido]-α-phenylacetamido}-3-cephem-4-carboxylic acid sodium salt.

To 100 ml. of formamide at room temperature there was added 12.73 g. of NaPESA (68 mmoles), followed by 5.73 g. of NaHCO$_3$ (68.2 mmoles) and the mixture was stirred for 30 minutes. Then, 21.695 g. of the solid 3-(dichloroacetyloxymethyl)-cephalosporin intermediate from Examples 1 or 2 above was slowly added (approximately 27.2 mmoles). After stirring the reaction mixture 15 minutes an additional 1.13 g. of NaHCO$_3$ was added (13.5 mmoles) and the resulting solution was stirred at room temperature for 3 hours. To the resulting dark solution there was added 100 ml. of acetone. The resulting solution cleared and was added over 5 minutes to a further 1000 ml. of acetone at 0° C. to precipitate the next intermediate product, 3-(4-β-sulfoethylpyridiniummethyl)-7-β-{D-α-[4-(4-methoxybenzyloxy)carbonyl]imidazole-5-carboximido]-α-phenylacetamido}-3-cephem-4-carboxylic acid, sodium salt plus excess NaPESA. The filtered solids were washed with three 100 ml. portions of acetone and dried to give 28.42 g. of the above-named 3-(4-sulfoethylpyridiniummethyl)-intermediate product as a tan solid. This intermediate 3-(4-sulfoethylpyridinium-methyl)-cephalosporin intermediate product was transferred for use in the next step of the process.

EXAMPLE 4

Illustrating use of above intermediate products for preparation of useful end product - here, 3-(4-β-sulfoethylpyrid-iniummethyl)-7-β-[D-α-(4-carboxyimidazole-5-carboxamido)-α-phenylacetamido]-3-cephem-4-carboxylic acid sodium salt.

(a) End Compound Preparation

To 71 ml. of formic acid was slowly added 28.32 g. of the Example 3, 3-(4-sulfoethylpyridinium-methyl)-cephalosporin intermediate, maintaining a temperature of 12° C. to 25° C. After the addition was complete the solution was stirred at room temperature for two hours and then cooled to +15° C., at which temperature 42 ml. of acetone was added. This resulting mixture was then slowly added to 668 ml. of acetone at room temperature, keeping the temperature below 20° C. The resulting slurry was stirred for 10 minutes and then filtered and the solid filter cake was washed with three portions of 71 ml. of acetone, and dried to give 19.22 g. of crude 3-(4-β-sulfoethylpyridinium-methyl)-7-β-[D-α-(4-carboxyimidazole-5-carboxyamido)-α-phenylacetamido]-3-cephem-4-carboxylic acid.

(b) Purification

To 78 ml. of $H_2O$ there was added 18.6 g. of the crude product from part (a) above. The pH of the resulting mixture was adjusted to 4.0 with saturated aqueous sodium carbonate solution. This resulting solution was added to 930 ml. of absolute ethanol over 3 minutes. The resulting slurry was slowly cooled to 0° C., stirred at 0° C. for 30 minutes and then filtered and the filter cake was washed once with 20 ml. of cold (0° C.) ethanol, and twice with 20 ml. portions of room temperature ethanol. After drying under $N_2$ pressure, there was obtained 13.67 g. of crude 3-(β-sulfoethylpyridinium-methyl)-7-β-[D-α-(4-carboxyimidazole-5-carboxyimidazole-5-carboxamido)-α-phenylacetamido]-3-cephem-4-carboxylic acid, sodium salt.

A column (2.5 cm. internal diameter) was packed with 250 ml. of AMBERLITE® XAD-7 brand of cross linked acrylic ester chromatography resin. Then 10.0 g. of the above part (b) crude 3-(β-sulfoethylpyridinium-methyl)-7-β-[D-α-(4-carboxyimidazole-5-carboxamido)-α-phenylacetamido]-3-cephem-4-carboxylic acid, sodium salt from the above aqueous ethanol precipitation was dissolved in 30 ml. of $H_2O$ and the pH of the resulting solution was adjusted to 3.12 with 1N HCl solution. The resulting solution was eluted on the XAD-7 ™ umn and fractions were monitored by HPLC, combining fractions rich in desired product. These combined fractions were concentrated to a weight of 51.5 g. To this concentrated aqueous solution there was slowly added 435 ml. of absolute ethanol at room temperature over 30 minutes. The slurry was then slowly cooled to 0° C., stirred 30 minutes at 0° C., and then filtered, and the filter cake was washed with 8 ml. of cold (0° C.) ethanol and twice with 8 ml. portions of room temperature ethanol. After drying under positive $N_2$ pressure the purified 3-(β-sulfoethylpyridinium-methyl)-7-β-[D-α-(4-carboxyimidazole-5-carboxamido)-α-phenylacetamido]-3-cephem-4-carboxylic acid, sodium salt was obtained as a white solid, 5.88 g., greater than 90% pure by HPLC.

This cephalosporin compound has been shown to possess high antibacterial activity, see *J. Antibiotics* 36, 242 (1983) and U.S. Pat. No. 4,217,450.

EXAMPLE 5

3-Chloroacetyloxymethyl-7-β-{D-α-[4-(4-methoxybenzyloxy-carbonyl)imidazolyl-5-carboxamido]-α-phenylacetamido}-3-cephem-4-carboxylic acid To a dry flask under $N_2$ atmosphere there was added 7.5 ml. of $CH_2Cl_2$, 0.5 ml. of THF and 620 mg. of 3-hydroxymethyl-7-β-{-α-[4-(4-methoxybenzyloxycarbonyl)imidazolyl-5-carboxamido]-α-phenylacetamido}-3-cephem-4-carboxylic acid. The resulting solution was cooled to 0° C. and 0.62 ml. of a potassium tert-butoxide in THF solution 1.6M in THF, 1.0 mmole of t-BuOK was added over 10 minutes. To the resulting cold solution there was added 24.4 mg. of DMAP, 0.168 ml. of triethylamine and 0.08 ml. of chloroacetyl chloride in 1.0 ml. of $CH_2Cl_2$. A second 0.168 ml. of TEA and 0.08 ml. of chloroacetyl chloride in 1.0 ml. of methylene chloride was then added. The resulting mixture solution was poured into 6.5 ml. of water containing 1.0 ml. of 1M sulfuric acid. To the resulting slurry there was added 2 ml. of hexane. The solids were filtered, washed with 20% V/V hexane in $CH_2Cl_2$ mixture and then with water. The washed, filtered solid was then dried to give 506 mg. of the hereinabove named 3-chloroacetyloxymethyl product. The NMR spectrum for the 3-chloroacetyloxymethyl- product was similar to that set forth in Example 1, part E, except that the 3'-$CH_2$ signal appeared at 4.9(m) and $CH_2Cl$ appeared at 4.1(s).

EXAMPLE 6

Product Prepared Using Potassium 2-Ethylhexanoate

To a dry flask under $N_2$ atmosphere there was added 7.5 ml. of $CH_2Cl_2$, 0.5 ml. of THF and 0.176 ml. of 2-ethylhexanoic acid. The solution was cooled to 0° C. and 0.65 ml. of a potassium tert-butoxide/THF (1.6M of t-BuOK) to make in situ the potassium 2-ethylhexanoate salt in solution. To this solution there was added 620 mg. of the same 3-hydroxymethyl- starting compound as named in Example 5. The resulting reaction mixture was processed as in Example 5 to give 537 mg. of the 3-chloroacetyloxymethyl- compound product of Example 5. The NMR spectrum was essentially identical to that for the product of Example 5.

EXAMPLE 7

Use of Chloroacetic Anhydride Instead of Chloroacetyl Chloride

A reaction procedure was conducted as set forth in Example 6, except that 0.1655 g. of chloroacetic anhydride in 1.0 ml. of $CH_2Cl_2$ was substituted for the chloroacetyl chloride used in Example 6. The reaction mixture was processed as in Example 6 to isolate, dry and obtain 531 mg. of the same 3-chloroacetyloxymethyl-product as named in Example 6. The NMR spectrum for this product was essentially identical to that for the Example 6 product.

EXAMPLE 8

3-Phenoxyacetyloxymethyl-7-β-{D-α-[4-(4-methoxybenzyloxy-carbonyl)imidazolyl-5-carboxamido]-α-phenylacetamido}-3-cephem-4-carboxylic acid.

A reaction was conducted according to the procedure described in Example 7 except that 0.138 ml. of phenoxyacetyl chloride in 1.0 ml. of $CH_2Cl_2$ was used in place of the chloroacetyl chloride there referred to. The reaction procedure was processed as described in Example 7 to isolate, dry and obtain 800 mg. of the hereinabove-named 3-phenoxyacetyloxymethyl-compound. The NMR spectrum was similar to that set forth in Example 1, but with the 3'-CH$_2$- moiety at 4.8(m), the -CH$_2$O-phenyl at 4.6(s) and phenyl resonances at 7.1 to 7.5(m).

EXAMPLE 9

3-(α-Chloropropionyloxy-methyl)-7-β-{D-α-4-(4-methoxybenzyloxycarbonyl)imidazolyl-5-carboxamido]-α-phenylacetamido}-3-cephem-4-carboxylic acid.

To a dry flask under N$_2$ atmosphere there was added 37.5 ml. of methylene chloride, 2.5 ml. of THF and 0.88 ml. of 2-ethylhexanoic acid. The solution was cooled to 0° C. and 3.25 ml. of potassium tertbutoxide in THF solution (1.6M of t-BuOK) was added to form in situ the potassium 2-ethylhexanoate salt base. To this mixture there was added 3.10 g. of the 3-hydroxymethyl-cephalosporin reactant, named in Example 1, part D, and 0.122 g. of DMAP and 0.84 ml. of triethylamine, followed by 3 ml. of CH$_2$Cl$_2$ containing 0.485 ml. of α-chloropropionyl chloride. When the addition was complete, a second 0.84 ml. portion of triethylamine and 3 ml. of CH$_2$Cl$_2$ solution containing 0.485 ml. of α-chloropropionyl chloride was added. The resulting reaction mixture was then added to 40 ml. of water containing 5 ml. of 1M sulfuric acid. Then 8 ml. of hexane were added. The reaction mixture was filtered and dried to obtain 2.29 g. of the hereinabove named 3-(α-chloropropionyloxymethyl)-compound. The NMR spectrum for this product was similar to that described in Example 1, but with the 3'-CH$_2$ reading at 4.9(m), the -CHCl at 4.4(q) and the CHCl-CH$_3$ at 1.5(d).

EXAMPLE 10

3-(4-Nitrobenzoyloxymethyl)-7-β-{D-α-[4-(4-methoxybenzyloxycarbonyl)imidazolyl-5-carboxamido]-α-phenylacetamido}-3-cephem-4-carboxylic acid.

To a dry flask under nitrogen atmosphere was added 10 ml. of methylene chloride and 0.62 g. of the 3-hydroxymethyl-cephalosporin reactant, named in Example 1, part D. After cooling the resulting mixture to −35° C., 0.68 ml. of 1.6M potassium tert-butoxide solution in THF is added. The resulting solution was warmed to −4° C., recooled to −35° C. and treated with (a) 0.155 ml., (b) 0.024 g. of triethylamine, (b) 0.024 g. of DMAP catalyst and (c) 0.190 g. of 4-nitrobenzoyl chloride in 1.8 ml. of methylene chloride. After addition of these components of the reaction mixture was completed, a second 0.155 ml. portion of triethylamine and 0.19 g. of 4-nitrobenzoyl chloride in 1.8 ml. of methylene chloride were added. The resulting reaction mixture was then added to 30 ml. of 1% sulfuric acid in water solution. The solid which resulted was filtered, washed with a 5% V/V hexane in 2-propanol mixture and dried to give 0.46 g. of the above-named 3-(4-nitrobenzoyloxymethyl)-compound. The NMR spectrum for this product was similar to the NMR spectrum for the Example 1 product, but with the 3'-CH$_2$ at 5.2(m) and aromatic resonances at 8.2(m).

EXAMPLE 11

3-(α,α-Dichloropropionyloxymethyl)-7-β-{D-α-[4-(4-methoxybenzoyloxycarbonyl)imidazolyl-5-carboxamido]-α-phenylacetamido}-3-cephem-4-carboxylic acid.

A reaction was conducted as described in Example 11 except that 0.115 ml. of α,α-dichloropropionyl chloride in 1 ml. of methylene chloride was used instead of 0.19 g. of p-nitrobenzoyl chloride in 1.8 ml. of methylene chloride. The reaction was processed by adding 30 ml. of hexane, filtering the solid which resulted and drying to give 1.02 g. of the above-named 3-(α,α-dichloropropionyloxymethyl)-cephalosporin compound, containing 2.0 equivalents of triethylammonium hydrochloride. The NMR was similar to that described for the Example 1 product, with the addition of NMR peaks for triethylammonium group at 1.2 (t) and 3.1 (q) and with the 3'-CH$_2$ at 5.0 (m) and CCl$_2$-CH$_3$ at 2.2 (s).

EXAMPLE 12

3-(Phenylsulfinyloxymethyl)-7-β-{D-α-[4-methoxybenzyl-oxycarbonyl)imidazolyl-5-carboxamido]-α-phenylacetamido}-3-cephem-4-carboxylic acid.

To a dry flask under nitrogen atmosphere was added 311 mg. of the 3-hydroxymethyl-reactant from Example 1, part D, and 5 ml. of methylene chloride. The mixture was stirred and cooled to −30° C. and then 0.324 ml of a 1.6M solution of potassium tert-butoxide solution in THF was added. After warming the mixture to 0° C., the solution was re-cooled to −30° C., and then 0.07 ml. of triethylamine, 0.012 g. of DMAP and then 0.06 ml. of phenylsulfinyl chloride in 1.0 ml. of methylene chloride were added. After the addition of these ingredients was completed another 0.07 ml. of triethylamine and 0.06 ml. of phenylsulfinyl chloride in 1.0 ml. of methylene chloride were added. The resulting reaction mixture was added to 20 ml. of hexane, solid was filtered and dried to give 580 mg. of the above-named 3-(phenylsulfinyloxymethyl)-cephalosporin product. The NMR was similar to that of the Example 1 product, with the addition of resonances for triethylammonium group at 1.2 (t) and 3.1 (q) and with the 3'-CH$_2$ reading at 4.8 (m) and aromatic peaks at 7.2-7.6 (m).

CHEMICAL STRUCTURES

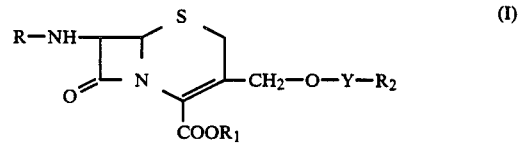
(I)

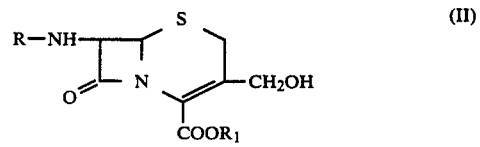
(II)

X—Y—R$_2$ (III)

(IV)

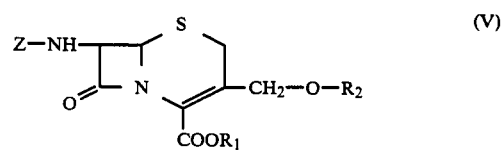
(V)

where Z is

-continued
CHEMICAL STRUCTURES

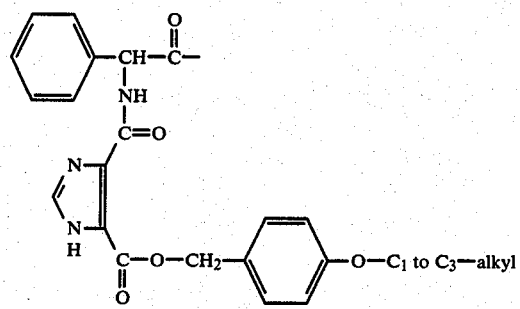

I claim:
1. A process which comprises reacting a compound of the formula

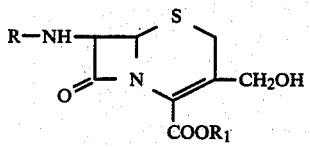 (II)

where
R is an amino protecting group;
$R_1$ is an alkali or alkaline earth metal cation;
with an activating acylating agent of formula (III)

$$X—Y—R_2 \quad (III)$$

wherein $R_2$ is the residue of an activating acyl ester forming group whose corresponding activating group acid has a pKa of less than 4.75;
Y is selected from the group consisting of —C(O)—, —S(O)$_2$— and —S(O)—;
X is chlorine or bromine,
in the presence of a 4-(tertiary amino)pyridine catalyst, and
in the presence of an acid absorbing tertiary amine base, present in an amount to absorb acid generated by the reaction,
at a temperature above about −78° C. to about 30° C.,
in a non-polar, liquid solvent containing a chlorinated $C_1$ to $C_2$ alkane, tetrahydrofuran, diethyl ether, hexane, heptane, octane, cyclohexane or a mixture thereof,
for a time sufficient to form a compound of the formula

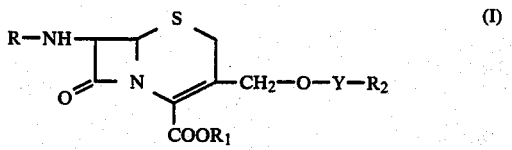 (I)

wherein R, $R_1$, $R_2$ and Y are as defined hereinabove.

2. A process according to claim 1 wherein the activating agent is an acyl halide of formula III wherein X is chlorine,
$R_2$ —Y— is a α-halogenated-$C_2$ to $C_6$-alkanoyl wherein the halogen is chlorine.

3. A process according to claim 1 wherein the 4-(tert-amino)pyridine catalyst is 4-(N,N-dimethylamino)pyridine.

4. A process according to claim 1 where the acid absorbing tertiary amine base is a tris ($C_1$ to $C_3$-alkyl)amine.

5. A process according to claim 1 wherein a potassium salt of a formula II cephalosporin compound is reacted with dichloroacetyl chloride in the presence of 4-(N,N-dimethylamino)pyridine catalyst and in the presence of an acid absorbing tertiary amine base present in amount at least stoichiometrically equivalent to the amount of dichloroacetyl chloride used in the process, at a temperature of from about −55° C. to 35° C. to form the corresponding 3-(dichloroacetyloxy methyl) cephalosporin compound (I).

* * * * *